(12) United States Patent
Sun (10) Patent No.: US 7,586,607 B2
(45) Date of Patent: Sep. 8, 2009

(54) POLARIZATION IMAGING

(75) Inventor: Gang Sun, Mendham, NJ (US)

(73) Assignee: Rudolph Technologies, Inc., Flanders, NJ (US)

( * ) Notice: Subject to any disclaimer, the term of this patent is extended or adjusted under 35 U.S.C. 154(b) by 114 days.

(21) Appl. No.: 11/678,407

(22) Filed: Feb. 23, 2007

(65) Prior Publication Data

US 2007/0247622 A1  Oct. 25, 2007

Related U.S. Application Data

(60) Provisional application No. 60/793,858, filed on Apr. 21, 2006, provisional application No. 60/844,297, filed on Sep. 12, 2006.

(51) Int. Cl.
*G01J 4/00* (2006.01)

(52) U.S. Cl. .................. 356/364; 356/237.2; 356/369

(58) Field of Classification Search ... 356/237.2–237.6, 356/364, 369
See application file for complete search history.

(56) References Cited

U.S. PATENT DOCUMENTS

| | | | |
|---|---|---|---|
| 2,947,212 A | 8/1960 | Woods | |
| 3,904,293 A | 9/1975 | Gee | |
| 4,469,442 A | 9/1984 | Reich | |
| 4,775,220 A | 10/1988 | Penkethman | |
| 4,806,776 A | 2/1989 | Kley | |
| 5,355,212 A * | 10/1994 | Wells et al. | 356/237.4 |
| 5,648,850 A | 7/1997 | Basler et al. | |
| 6,512,578 B1 | 1/2003 | Komatsu et al. | |
| 6,791,680 B1 | 9/2004 | Rosengaus et al. | |
| 6,930,813 B1 * | 8/2005 | Liphardt et al. | 359/237 |
| 7,012,684 B1 * | 3/2006 | Hunter | 356/237.5 |
| 7,164,475 B2 | 1/2007 | Fairley et al. | |
| 2003/0112428 A1 * | 6/2003 | Oomori et al. | 356/237.3 |
| 2006/0214673 A1 | 9/2006 | Tamai | |
| 2007/0013902 A1 | 1/2007 | Backhauss et al. | |

OTHER PUBLICATIONS

PCT Search Report (mailed Sep. 16, 2008); 8 pgs.

* cited by examiner

*Primary Examiner*—L. G. Lauchman
*Assistant Examiner*—Iyabo S Alli
(74) *Attorney, Agent, or Firm*—Dicke, Billig & Czaja, PLLC (57) ABSTRACT

A system and method for inspection a substrate for various defects is herein disclosed. Polarizing filters are used to improve the contrast of polarization dependent defects such as defocus and exposure defects, while retaining the same sensitivity to polarization independent defects, such as pits, voids, cracks, chips and particles.

11 Claims, 5 Drawing Sheets

POLARIZATION IMAGING

CROSS-REFERENCE TO RELATED APPLICATIONS

This application claims priority under 35 U.S.C. §119(e)(1) to U.S. Provisional Patent Application Ser. No. 60/793,858, filed Apr. 21, 2006, entitled "Polarization Imaging," and U.S. Provisional Patent Application Ser. No. 60/844,297, filed Sep. 12, 2006, entitled "Polarization Imaging,"; the teachings of both of which are hereby incorporated by reference.

TECHNICAL FIELD OF THE INVENTION

The present invention relates generally to inspection and metrology tools for used to ensure quality and improve yield in semiconductor device manufacturing processes.

BACKGROUND OF THE INVENTION

In lithographic semiconductor device fabrication processes, it is imperative that a stepper precisely focus an image of a reticle on a semiconductor substrate or wafer. Where the image of the reticle is out of focus, a state also known as defocus, the structures of the resulting semiconductor device may be of the incorrect size and form. For example, the edges of the resulting structures may be relatively diffuse and indistinct, having rounded or undercut surfaces in lieu of a more desired, often rectilinear geometry. This state of defocus often leads to poor function and/or inoperability in the semiconductor device in question. Measurement of defocus is therefore an important means for allowing semiconductor device manufacturers to ensure that a stepper consistently focuses a reticle image on a wafer, thereby enabling larger and more profitable yields from the manufacturing process.

Another problem common to the formation of semiconductor devices is that of exposure defects. Where the exposure of a photo resist layer to light falls outside a range of acceptable light dosages, the features that are to be formed on the semiconductor substrate may be formed incorrectly. Accordingly, it is also important to identify exposure defects where they exist.

In addition to inspecting a substrate or wafer for exposure or defocus defects, it is important to inspect substrates and wafers for process or material related defects commonly referred to as "macro" defects. Macro defects are often defined as chips, cracks, scratches, pits, delaminations, and/or particles that appear on a substrate that have a dimension of about 0.5 u to 10 u in size. Such defects can easily cause a failure in a semiconductor device and can significantly reduce the yield of a manufacturer of such devices. Note that the sizes of macro defects may depart up or down from the size range stated above, which merely defines a nominal size of such defects.

Traditionally, macro defects have been inspected using dedicated inspection systems that have not been able to readily or reliably identify the presence of exposure or defocus defects. Exposure and defocus defects are usually identified using optical critical dimension (OCD) techniques on any of a number of precision metrology tools such as ellipsometers, reflectometers and scatterometers. It would be desirable to combine the functions of identifying the presence of exposure and defocus defects with inspection of substrates for macro defects wherein the same optical system is used for both functions.

SUMMARY

One embodiment of an inspection system for identifying defects on a substrate includes a light source that directs light onto a substrate that is to be inspected. A first polarizing filter, or polarizer, is positioned between the light source and the substrate. A second polarizing filter, or analyzer, is positioned between the substrate and an optical sensor that receives light reflected from the substrate. The polarizer and analyzer, are angularly arranged with respect to one another such that an image intensity of an image captured by the optical sensor is at least partially correlated with the presence of polarization dependent defects on the substrate under test. Polarization dependent defects include, among other things, defocus and exposure defects. Defects having a main dimension of approximately the wavelength of incident light or smaller that are not defocus or exposure defects may also be identified.

The light source may be of any useful type including, but not limited to, a broadband incandescent light or a laser. Either of these light sources may strobe and may be positioned to direct light on the surface of the substrate at any useful angle of incidence, including a normal angle of incidence. Lasers may be of a fixed, monochrome variety or may be arranged to output light at several different nominal wavelengths.

Where strobe illumination is used, the strobe will flash on and off in a sequence that at least partially correlates with the velocity at which a substrate is moved with respect to the inspection system. This permits the inspection system to reliably capture images of the substrate at the appropriate locations.

The optical sensor or imager may be a monochrome charged capacitance device (CCD). In some instances, the optical sensor may be a color imager of the Bayer type or a three-chip design. In yet other instances, one or more light source and/or color filters may be used in conjunction with a monochrome optical sensor to obtain color data from the substrate. Both area scan and line scan optical sensors may be used.

In addition to defocus and exposure defects, other types of defects may be identified. These other defects may include pits, voids, chips, cracks, particles, and scratches.

Inspection systems according to the present invention are put into operation by first arranging the light source to direct light onto the substrate. The first polarizing filter is positioned between the light source and the substrate and the optical sensor is placed to receive light reflected from the substrate. The second polarizing filter is placed between the substrate and the optical sensor and such that the first and second polarizing filters are at a selected relative angle with respect to one another. The inspection system is then used to capture images of the substrate and comparative data is generated from these images to identify the existence of exposure and/or defocus defects on the substrate, if any. Arranging the polarizing filters to capture the required images may involve rotating the first and second polarizing filters together to a desired inspection angle whilst maintaining the selected relative angle therebetween.

Comparative data may be obtained by first generating a differential image for each captured image and then averaging pixel intensity differences of the respective differential images over the entire differential image to obtain an average image intensity for each differential image. The average image intensity of each captured image is evaluated with respect to a predetermined threshold to determine the existence of at least one of exposure and defocus defects on the substrate, if any.

Calibration of the output of the optical sensor with respect to known levels of at least one of an exposure and a defocus defect in a substrate is used to determine appropriate defocus and exposure defect levels. In one embodiment calibration involves capturing a plurality of images of a calibration substrate, wherein each image is subject to a known degree of defocus and exposure defects. As described above, a differential image is generated for each captured image and the pixel intensity differences of the differential images are averaged over the entire differential image to obtain an average image intensity. The average image intensity values for each captured image having a known degree of defocus and exposure defect are recorded. A user may select any recorded average image intensity value indicative of a particular degree or magnitude of defocus and/or exposure defects as a threshold, may interpolate between such recorded values or may simply use the recorded values as a starting point to which modifiers specific to the product are applied. It is entirely up to the user of an inspection system to define suitable thresholds for defocus and/or exposure defects.

Generating a differential image may involve averaging a plurality of captured images on a pixel by pixel basis to obtain an averaged image. This averaged imaged is then subtracted from each captured image, on a pixel by pixel basis to produce a differential image that can also be thought of as an array of pixel intensity values or as an array of pixel intensity value differences.

Inspection of a substrate for defocus and/or exposure defects may take simultaneous with inspection for other defects such as pits, voids, chips, cracks, particles, and scratches. Alternatively, inspection for these respective types of defects may take place successively or even in a time shifted manner, i.e. at times that are significantly separated from one another.

In another embodiment of the present invention, image analysis techniques such as spatial pattern recognition (SPR) techniques may be used to analyze a differential image to identify the boundaries of layers on a substrate. Note that layer boundaries such as the aforementioned ones may be part of layers that are an intentional part of the substrate or may be related to residues that are not intentionally part of the substrate, i.e. the layers may be contaminants of one type or another.

DETAILED DESCRIPTION OF THE INVENTION

In the following detailed description of the invention, reference is made to the accompanying drawings that form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention. The following detailed description is, therefore, not to be taken in a limiting sense, and the scope of the present invention is defined only by the appended claims and equivalents thereof.

The present invention involves a method and apparatus for determining the presence of exposure and defocus lithographic defects in a semiconductor substrate by measuring a change in the polarization of light reflected from the surface of the substrate. To simplify the following discussion, the term "defocus" will be used herein to denote both exposure and defocus defects, though it is to be understood that a given substrate may suffer from the one defect or the other or both. Further, the term "defocus" shall be construed broadly to encompass any defect or undesirable feature of a substrate under inspection that has characteristic results similar to exposure and/or defocus defects and which may be identified or otherwise characterized by the inspection system of the present invention. In general, defocus defects are polarization dependent features, that is, defocus defects will cause a change in the polarization state of light reflected therefrom, though it is understood by those skilled in the art that other aspects of defocus defects may affect the nature and extent of such polarization changes.

As used herein, the term "substrate" shall be construed to include any material or structure that may be inspected by the inspection system of the present invention. Specifically, the term "substrate" shall be construed to include, among other things, semiconductor wafers of any construction or form or material, including, but not limited to, whole wafers, unpatterned wafers, patterned wafers, partially patterned wafers, broken wafers that are wholly or partially patterned, broken wafers that are unpatterned, sawn wafers in any form and on any support mechanism, including film frames, JEDEC trays, Auer boats, die in gel or waffle packs, multi-chip modules often referred to as MCMs, etc. The terms "substrate" and "wafer" may be used interchangeably herein.

The term "macro defect" as used herein will include all unintentional features that appear on a substrate that are essentially polarization independent. As noted above, macro defects are traditionally described as being chips, cracks, pits, particles, scratches and the like. Note that in some instances, the size of macro defects may approach the wavelength of the incident radiation being used for inspection purposes. In these instances, macro defects may have an effect on the polarization state of light reflected therefrom.

Figure 1:
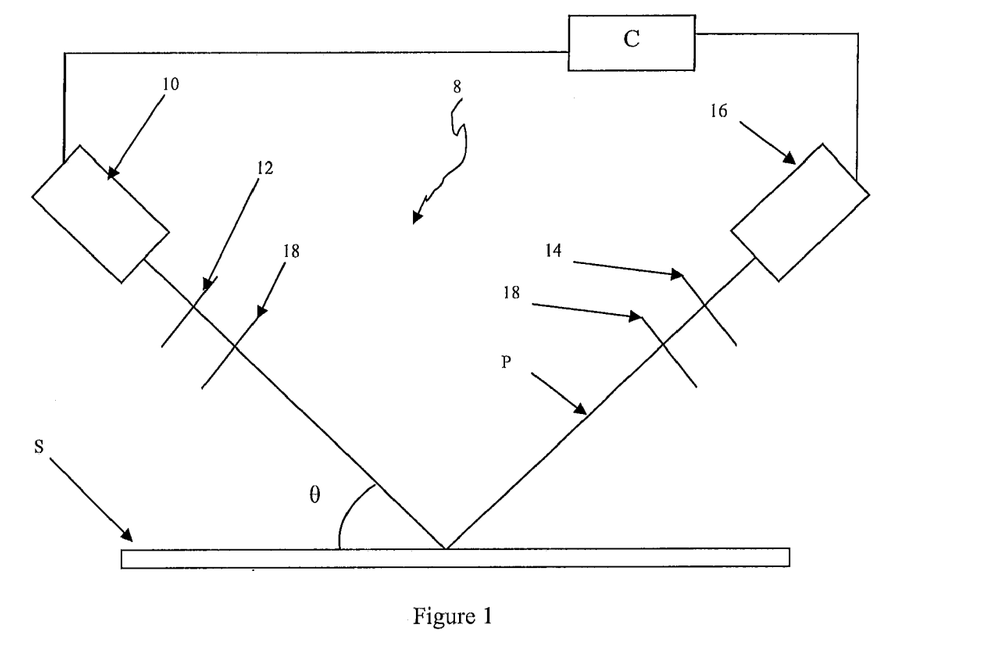
FIG. 1 is a schematic view of one embodiment of an imaging system of the present invention having a nominal angle of incidence other than 90°.

With reference to FIG. 1, one embodiment of an imaging system 8 includes an illuminator 10, a polarizer 12, an analyzer 14, and an optical sensor 16. The illuminator 10 directs light along optical path P onto the polarizer 12, which transmits substantially only light having a predetermined polarization angle. The light transmitted by the polarizer 12 is then incident upon a substrate S. In one embodiment, the substrate S is a silicon wafer or a portion thereof having structures formed thereon. In some embodiments, these structures form one or more semiconductor devices on the substrate S. Other mechanisms and structures may also be formed on the substrates S.

As can be seen in FIG. 1, optical path P is at a non-normal angle of incidence with respect to the substrate S. In some embodiments the illuminator 10, polarizer 12, analyzer 14, and optical sensor 16, as well as other associated optical elements such as objectives and the like, may be mounted so as to permit the angle of incidence of light on the substrate S to be modified. Mounting mechanisms of the type that would be useful in modifying the angle of incidence of light in the system 8 are known to those skilled in the art and may include a mounting plate(s) to which the optical elements of the system 8 are mounted, the mounting plate(s) being rotatable by a rotation means that can be one or more actuators. The angle of incidence may be essentially fixed (as shown) or may be modified for each product set-ups. Further, in some embodiments, the angle of incidence may be modified during inspection, as needed.

The illuminator 10 may be of any useful type, including a broadband white light, a laser having a fixed wavelength output, a laser arranged to output multiple wavelengths, or a plurality of lasers arranged to direct light along the optical path P. The intensity required of the illuminator may vary depending on the application to which the system 8 is directed. In some applications, a high intensity illumination is required and conversely, in others, relatively lower intensities are required. The illuminator 10 may be arranged to provide substantially constant output or may be arranged to strobe so as to freeze the motion of a substrate S in the system 8, thereby allowing the rapid capture of images of the substrate S.

The light incident upon the substrate S is reflected therefrom and this reflected light is incident upon an analyzer 14 which, being a polarizing optical element similar to polarizer 12, passes only that light having a predetermined polarization angle. What light passes through analyzer 14 is incident upon optical sensor 16, which captures an image of the substrate S. Optical sensor 16 is in one embodiment a two dimensional electronic optical sensor such as charge-coupled device (CCD), though any device capable of producing a two dimensional array of pixel intensity values on a grayscale or color basis, such as a line scan or time delay integration imaging (TDI) device or a CMOS optical sensor array, may be used. In one embodiment, the optical sensor 16 is a monochrome optical sensor wherein each pixel of the optical sensor's 2D array of pixels registers a grey scale value of 0-256, which pixels, taken together represent an image of the substrate S. Where a monochrome optical sensor is used, one or more color filters 18 may be positioned in the optical path P between the illuminator 10 and the optical sensor 16 to pass only light within the range of wavelengths to which the color filter corresponds. In another embodiment, the optical sensor may be a color optical sensor of the Bayer type or a three-chip color sensor having separate optical sensors, each dedicated to a separate color, e.g. one sensor for red light, one sensor of blue light, and one sensor for green light.

Those skilled in the art will understand that the basic elements of the system 8 described herein above may be used in conjunction, or not, with other optical elements including, but not limited to optical filters, lenses, mirrors, retarders and modulators. One inspection system that may be adapted for carrying out the present invention is marketed by Rudolph Technologies, Inc. of Flanders, N.J. under the trade name WaferView™. Further, it is to be understood that the system 8 may be arranged to carry out multiple functions, these multiple functions being carried out in simultaneous or in temporally spaced arrangements. For example, the system 8 may be adapted to carry out an inspection for macro defects as well as an inspection for defocus defects. Further, the system 8 can be arranged to carry out an inspection for macro defects followed by an inspection for defocus defects, or vice versa, or may carry out both inspections simultaneously.

Color filters 18 may be used in the system 8 as shown schematically in FIG. 1. One or more color filters 18 may be placed between the polarizer 12 and the substrate S, between the substrate S and the analyzer 14, between the illuminator 10 and the polarizer 12, or between the analyzer 14 and the optical sensor 16. In one embodiment, the color filter 18 may be a filter wheel of a type known in the art wherein one of a group of color filters is affixed to a rotating wheel placed in the optical path P such that the color filters 18 are selectively positioned across the optical path P. In another embodiment, a removable filter holder may be placed in the optical path P to permit different color filters to be placed in the optical path P. In yet another embodiment, a fixed color filter may mounted in the optical path P. It is to be understood that any filter media or mechanism suitable for selectively passing a predetermined wavelength or range of wavelengths may be used as a color filter.

In some embodiments, it is desirable to separate the output of the optical sensor 16 with respect to predetermined color channels wherein "color channel" is defined as a predetermined wavelength or range of wavelengths. Separation of color channels may be accomplished, as suggested above, by the use of color filters, by the use of color optical sensors that incorporate directly the ability to distinguish between respective color channels as do three-chip optical sensors and Bayer optical sensors, or by using an illuminator 10 that outputs light within a pre-selected range of wavelengths. It should be understood that some substrates S may be partially or wholly transmissive with respect to certain ranges of wavelengths or colors. By way of example only, a given substrate S may transmit or destructively interfere a majority of all incident blue light having wavelengths centered around 475 nm, but reflect a large portion of the red light having wavelengths centered around 700 nm that is incident on the substrate S. In this example, it may be useful then to be able to use the signal output by the optical sensor 16 that results from the red light incident on the optical sensor 16. The use of data relating to a respective color channel will depend on what features are being examined in the inspection being undertaken with the system 8. In some embodiments, certain semiconductor substrates, also known as products, will tend to have features that reflect light in a known manner and accordingly, an inspection system 8 may be set up specifically for a given product to optimize the inspection of the product.

Figure 2:
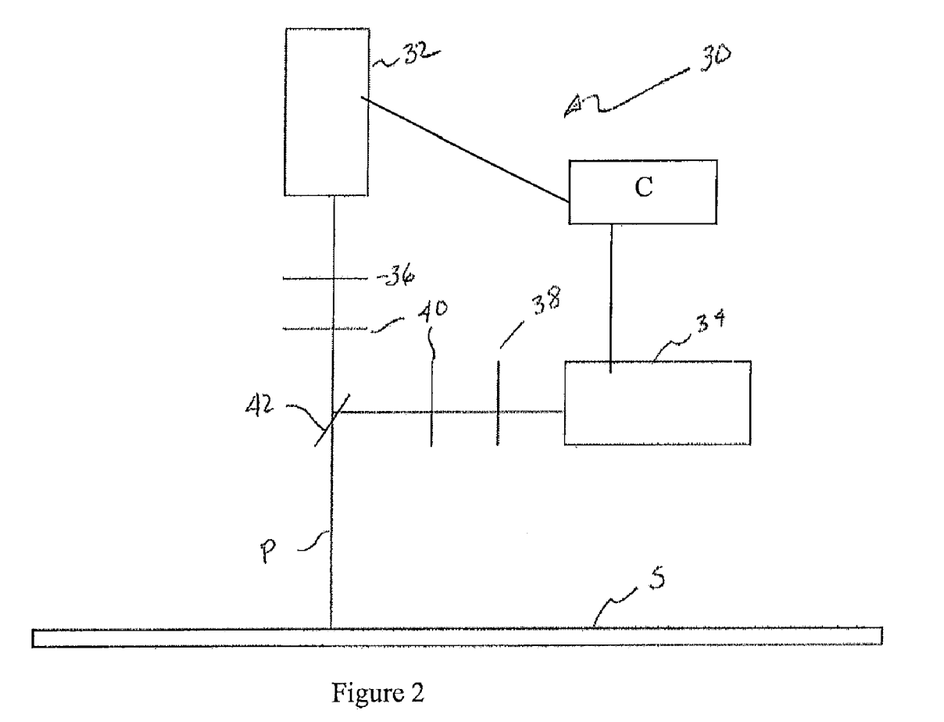
FIG. 2 is a schematic view of one embodiment of an imaging system of the present invention having a nominal angle of incidence of substantially 90°.

FIG. 2 illustrates another embodiment of the present invention wherein an inspection system 30 has an illuminator 32 that directs light along optical path P though polarizer 36, filter 40 (optional), and beam splitter 42 onto substrate S in a substantially normal arrangement. Light reflected from substrate S on path P is directed by beam splitter 42 through filter 40 (optional) and analyzer 38 to optical sensor 34. Systems 8 and 30 are, aside from the presences of a beam splitter and differences in the angle of incidence, substantially similar. In this embodiment, optical path P is substantially normal to the substrate S.

It has been observed that defocus defects will modify the reflectivity of a substrate S as defocus defects will modify the geometry of the structures formed on a substrate S. Other factors that will modify the reflectivity of a substrate S are the properties of other film layers and the wavelength, polarization, and angle of light incident upon the substrate. Using an inspection system according to various embodiments of the present invention, e.g. systems 8 or 30, it is possible to distinguish those reflectivity changes that result from defocus defects and to do so in a rapid and reliable manner.

In general, light from an illuminator 10, 32 is polarized to a predetermined angle P by a polarizer 12, 36 and incident upon a substrate S at a specified angle θ.

Upon reflection, the substrate S will modify the polarization state of the incident light in relation to a number of characteristics thereof and specifically defocus. From this modification of the polarization information concerning defocus defects in the substrate S can be obtained. The reflected light passes through analyzer 14 and is incident upon optical sensor 16. The analyzer 14, when arranged as described in more detail hereinbelow, helps ensure that the data obtained from the optical sensor 16 includes information concerning both the amplitude and the polarization change of the reflected light and particularly information concerning the presence of defocus defects on the substrate S.

In one embodiment, the light incident upon the substrate S is linearly polarized by polarizer 12, 36 as this often presents the simplest solution to the inspection problem at hand. In other embodiments, incident light is elliptically or circularly polarized, as needed. By setting the analyzer 14, 38 at an angle A with respect to the polarizer 12, 36, the light that reaches the optical sensor 16, 34 may be modulated. The angle between the polarizer 12, 36 and the analyzer 14, 38 is given as P-A.

Figure 3:
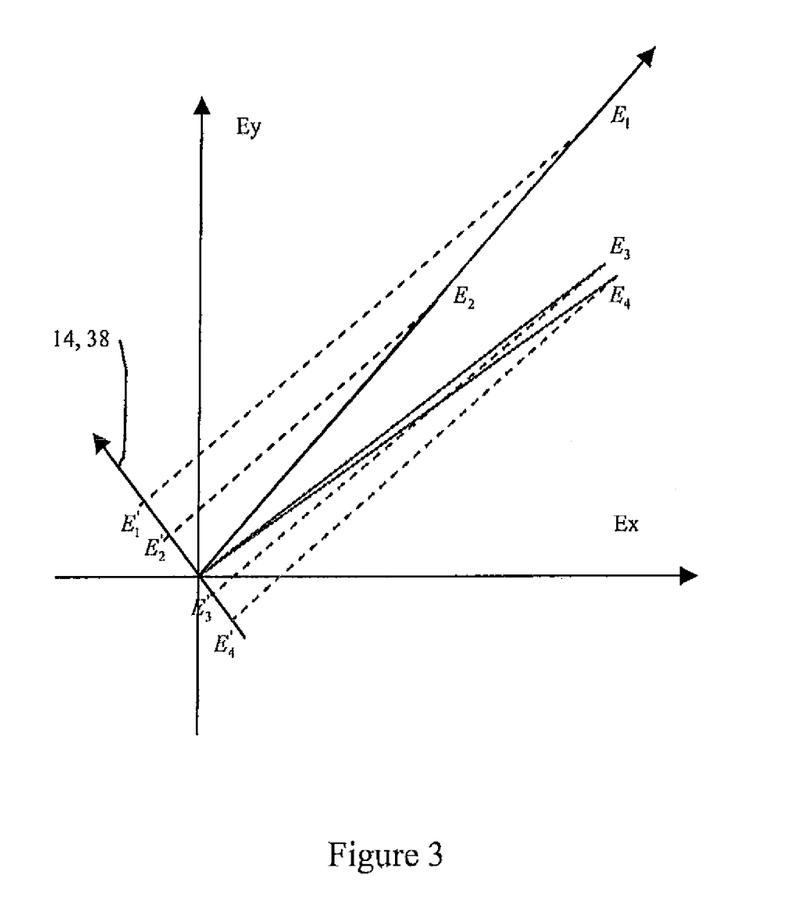
FIG. 3 is an illustration, in vector form, of the relative components of reflected light reflected from a substrate.

Referring now to FIG. 3, in general, when light is reflected from the substrate S, portions of the incident light, $E_P$, will be reflected differently than other portions of the incident light. A portion of the incident light $E_P$ is reflected from polarization independent features on the substrate S surface without any significant modification in its polarization as illustrated in FIG. 3 at $E_1$ and $E_2$. Some examples of such features that may be found on a semiconductor substrate S include, but are not limited to, bright and dark appearing defects in the substrate S such as chips, cracks, scratches, pits, voids, and particles. Another portion of the reflected incident light, $E_3$, is reflected from polarization dependent features formed on the substrate S that are arranged in such a way that they will modify the polarity of the incident light. Some examples of the polarization dependent features or structures found on a semiconductor substrate S include, but are not limited to, line structures, conductors, interconnects, vias and streets. Yet another portion of the incident light reflected from the surface of the substrate S is reflected by features or structures that modify the polarization of the reflected light and which are also subject to defocus defects. This light, $E_4$, has a polarization state that differs from $E_3$. Structures that reflect light $E_4$ may be structurally similar or identical to the nominal structures from which light $E_3$ described above is reflected except for the fact that they are subject to defocus defects, the magnitude of which will affect the intensity of light $E_4$.

Figure 4:
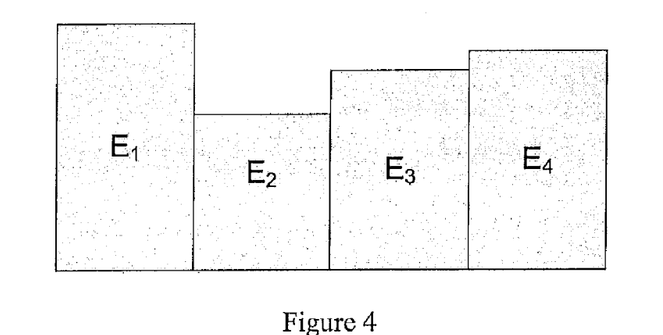
FIG. 4 is a chart showing the relative components of reflected light before being passed through an appropriately arranged analyzer.
Figure 5:
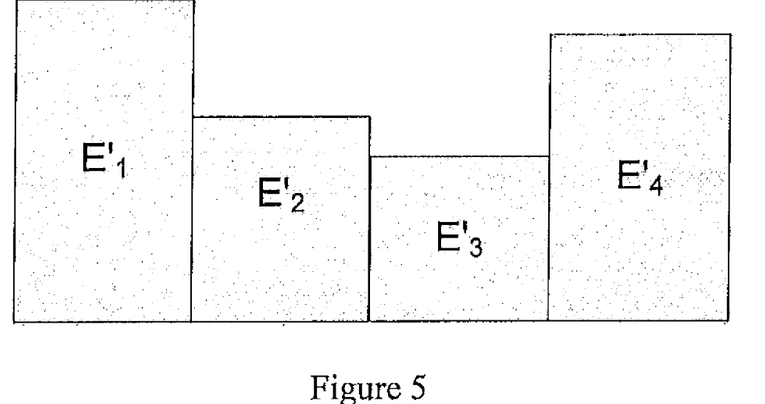
FIG. 5 is a chart showing the relative components of reflected light after having been passed through an appropriately arranged analyzer.

Referring to FIG. 4, it can be seen that for light that has not passed through the analyzer 14, 38, there is little contrast between the intensity of reflected light $E_3$ and $E_4$. As can be appreciated, it is difficult to identify defocus defects under these circumstances. However, once the reflected light $E_1$, $E_2$, $E_3$, and $E_4$ is passed through a properly arranged analyzer 14, 38, to obtain light signals $E'_1$, $E'_2$, $E'_3$, and $E'_4$, the contrast level between light signals $E'_3$, and $E'_4$ is sufficient to obtain useful information concerning the presence of defocus defects. See FIG. 5.

Figure 6:
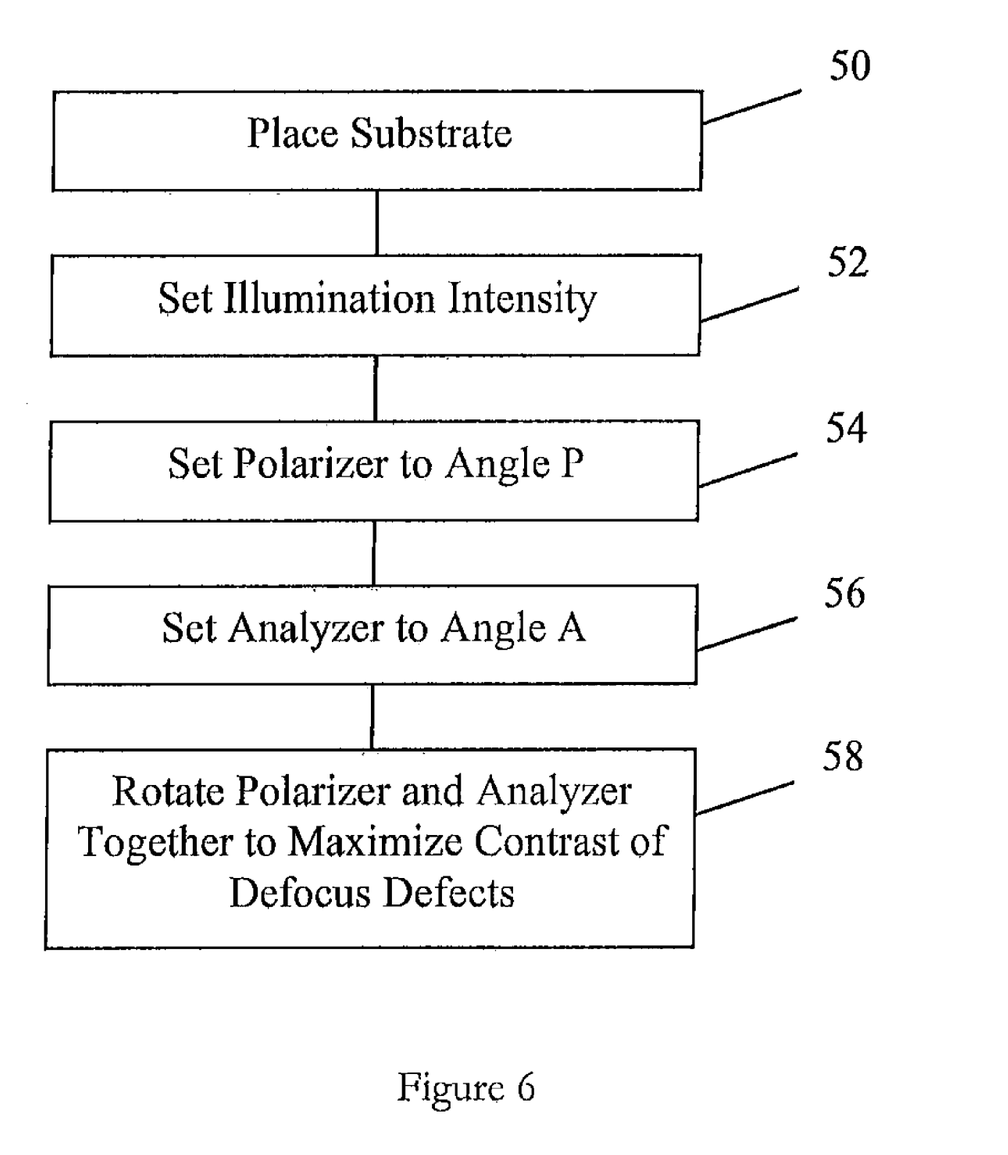
FIG. 6 is a flow chart illustrating a method of setting up an inspection system for inspection.

In one embodiment, the angle P-A between the polarizer 12 and the analyzer 14 is determined experimentally. Referring now to FIG. 6, with a test substrate S positioned in the system 8 for inspection (step 50), the illuminator 10, which is in one embodiment a strobe illuminator, is set to a predetermined illumination level (step 52) that is preferably near the top end of its intensity output, but may be of any suitable intensity. Light $E_P$ from the illuminator or light source 10 is directed through the polarizer 12 and onto the substrate S. Next, the polarizer 12 is set to an angle P (step 54). In one embodiment, the polarizer 12 is angularly oriented substantially perpendicular to any linear structures present on the substrate S. As will be understood, where the substrate S is a semiconductor wafer having semiconductor devices formed thereon (in any state of completeness), such structures typically, but not always, have significant linear features. Reflected light ($E_1$, $E_2$, $E_3$, and $E_4$) is passed through the analyzer 14 to obtain light signals $E'_1$, $E'_2$, $E'_3$, and $E'_4$ on optical sensor 16. In instances where there is no discernable orientation to linear structures on a substrate S or where the substrate S has no linear structures formed thereon, an arbitrary angle P may be chosen for polarizer 12.

The analyzer 14 is next rotated to an angle A (step 56) such that sufficient illumination reaches the optical sensor 16 to permit inspection of the substrate S for macro or polarization independent defects as described in U.S. Pat. Nos. 6,324,298, 6,487,307 and 6,826,298, which are owned jointly herewith and which are hereby incorporated by reference. Note that the analyzer 14 will be considered to be at the correct angle A when the illumination not only allows for inspection of the substrate S for defects, but also does so with a signal to noise ratio that permits for an inspection of sufficient quality to satisfy an end user of the system 8 that significant errors such as false positives and missed defects do not occur in the inspection. The signal to noise ratio of the system 8 is determined by analyzing the output of the optical sensor 16 in a known manner.

Once the angles P and A at which the polarizer and analyzer are positioned are known, the polarizer and analyzer are rotated together through a series of inspection angles (step 58), keeping the relative angle between the polarizer and analyzer (P-A) substantially constant, to a desired angular position with respect to the substrate S that will provide the necessary contrast between light signals $E'_3$ and $E'_4$ as described above. During rotation of the polarizer 12 and the analyzer 14, the intensity of light incident upon the optical sensor 16 is recorded. Light intensities at the optical sensor 16 are recorded for each of the inspection angles or positions through which the polarizer 12 and analyzer 14 are rotated. In one embodiment, the polarizer and analyzer 14 are rotated in a more or less continuous manner and the position of the polarizer and analyzer and the light intensity present at the optical sensor 16 are recorded in small increments of rotation of the polarizer and analyzer. Analysis of the data obtained during rotation of the polarizer and analyzer is performed to identify the optimal inspection angle or position for the polarizer and analyzer with respect to the contrast between reflected light $E'_3$ and $E'_4$.

The process of identifying an optimal setting for angles P and A may be manual, wherein a user of the system 8 rotates the polarizer 12 and analyzer 14 through a selected range of angles while the optical sensor 16 records image data which is processed by a computer C of a suitable type to determine the optimal angle P-A. Alternatively, and preferably, the polarizer 12 and analyzer 14 will be automated such that the aforementioned computer can control the rotation thereof while it records data from the optical sensor 16 at various angles P-A. Automation of polarizers and analyzers is well known to those skilled in the art. As suggested above, the process of determining an optimal angle P-A angle between the polarizer and analyzer may require multiple iterations, both before and after the steps that are described immediately hereinbelow. For example, once an entire calibration/set-up process is completed, it may be useful to run the entire calibration/set-up process multiple additional times to determine whether the resulting system set-up is optimal.

Once the system 8 has been appropriately set up as described in conjunction with FIG. 6, inspection for defocus defects and if desired, other defects, may take place. First, however, the system 8 must be calibrated. Calibration is preferably carried out using a focus exposure matrix (FEM) wafer. An FEM is a substrate on which a number of patterns or structures have been formed, each with a different focal position and exposure (exposure) time. An FEM is commonly created as part of calibrating a photolithography tool for the production of semiconductor devices. The FEM embodies structural changes in the patterns or structures formed on the substrate S that result from changes in focal position and exposure. Defocus and exposure data obtained from the FEM is used as a comparator during inspection of substrate S. Note that the patterns formed on the FEM may be different than those formed on the substrates S under test, but are preferably the same.

As the method of obtaining defocus data is substantially the same for calibration purposes as it is for inspection purposes, the method of obtaining defocus data for calibration purposes will be described as part of the inspection process. Differences between calibration and inspection procedures will be noted where appropriate.

During inspection, a substrate S of the type that is to be inspected is obtained and placed on a wafer support or top plate (not shown) that moves the substrate S relative to the optics of the inspection system 8 in a known manner. Substrates S (product or FEM) are in some embodiments inspected piecewise. In one embodiment wherein the substrate S is a wafer on which semiconductor devices are formed, the inspection of the substrate S is carried out on a die level basis, that is, images of the individual die on the substrate S are imaged by sensor 16 and those images are processed as described hereinbelow. In other embodiments, inspection is carried out on a field of view basis. The optics of a system 8 will be arranged to capture images of a field of view whose size may differ from that of an individual die or that of an individual stepper shot. Where the field of view of a system 8 is smaller than an individual die, multiple fields of view may be stitched together to create composite images of individual die. The same stitching technique may be used to form a composite image of an entire stepper shot. It is to be understood that stitching images to form a composite image is a technique that is well known in the art.

In other embodiments where the field of view is larger than an individual die or larger than a stepper shot, the resulting images may be cropped to show one or more die or stepper shots. It is generally useful to not crop a larger image so as to include multiple die from separate stepper shots as those die created by a first stepper shot may be acceptable while those die created by a second stepper shot may be defective. Cropping an image is a technique well known to those skilled in the art.

In yet other embodiments, inspection of the substrate S is accomplished by first capturing an image of an entire substrate S. Where the substrate S is relatively small, this may be capture using a system 8 operating on an area scan principle. Where the substrate is larger than the field of view of an area scan system 8, multiple images of the substrate S may be obtained and stitched together as suggested above. Stitching may be used in conjunction with line scan as well as area scan type inspection systems 8 as will be readily appreciated by those skilled in the art.

Once the appropriate polarizer/analyzer angle P-A is obtained as described above, images of individual die on the substrate S are captured by the optical sensor 16 (step 60). See FIG. 7. The calibration and inspection processes described hereinbelow will be described as taking place on a die by die basis, though it is to be understood that other bases may be used. The die on the substrate S that are imaged may be selected by a user who determines that the die are sufficiently free of defects such as chips, cracks, pits, color variation, particles or the like to form a model. This determination is entirely up to the user of the system 8 and can vary greatly depending on the nature and intended use of the product on the substrate S. For example, a user inspecting substrates S having semiconductor devices formed thereon that are intended for use in pacemakers would likely impose very stringent standards concerning the number of defects on a die that is to be used for the purpose of creating a model. Conversely, a user inspecting substrates S having identical semiconductor devices formed thereon that are intended for use in an inexpensive and essentially disposable consumer product would likely be willing to accept a higher number of defects in die that are to be used for the creation of a model. In short, it is up to the judgment of a user of a system 8 as to what defines a 'good' die for the purposes of creating a model. While it is envisioned that images of all 'good' die on a substrate S may be obtained for the purpose of creating a model, it is typically the case that only a statistically significant number of 'good' die; this number is generally less than the total number of 'good' die and may be on the order of about 10-15. At a minimum, die having no more than a modest number of random, relatively unobtrusive defects should be chosen as small, random defects will not likely not have a significant effect on inspection if a statistically significant sample of such die are sampled, it being understood that large, non-random defects will be more likely to skew an inspection process.

Figure 7:
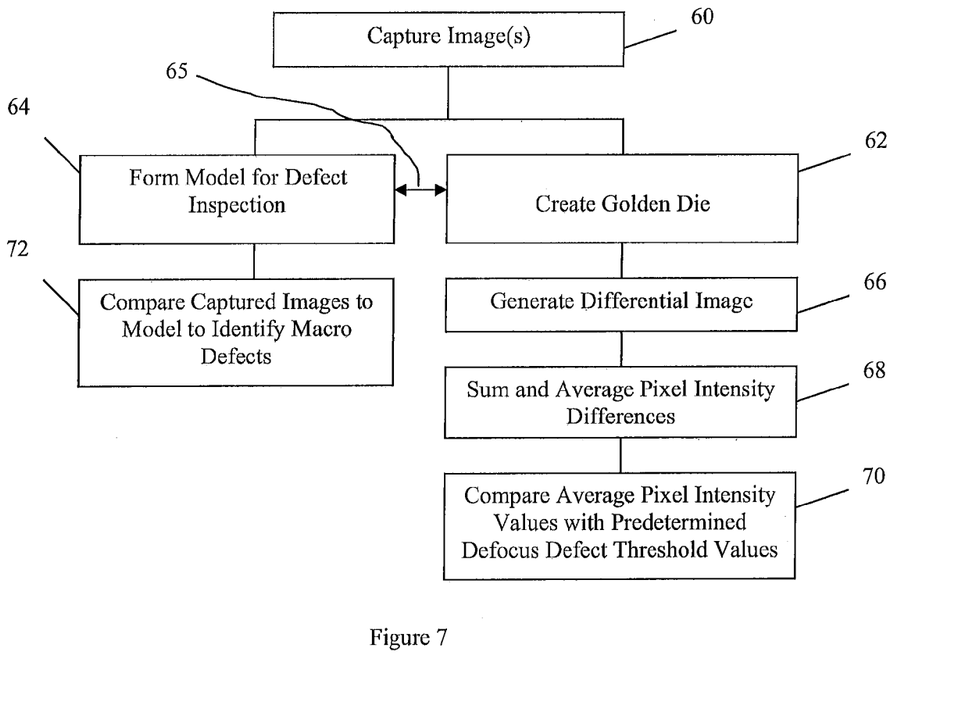
FIG. 7 is a flow chart illustrating a method of inspecting a substrate.

Automated methods may also be used to obtain a useful model. For example, a computer C that controls the system 8 may randomly select a statistically significant number of die and capture images thereof. These images are then used to form a model which is used to inspect the individual images that formed the model. Where a selected die is found to be defective under the user-selected criteria, the defective image will be replaced by an image of another randomly selected die. This process will be iterated until a suitable model is created. Note that models created manually or automatically may remain static, i.e. will not change over time, or may be modified over time by adding new, good die to the model as inspection progresses.

As the term "model" may have different meanings to different persons of skill in the art, it should be made clear that as used herein, the terms "golden die" or "golden reference" are used to describe an image whose constituent pixels have intensity values obtained by summing the corresponding pixel values of a number of die and obtaining an average of those values. Accordingly, the golden die is simply an image of averaged die. The term "model" is broader than the terms "golden die" or "golden reference" and in some instances, will not incorporate or use golden die or golden reference information.

A golden die is used in one embodiment of defocus inspection (step 62).

Similarly, golden die may form at least part of the basis for a model used in macro defect inspection. Generally, however, models used in macro defect inspection move beyond a simple golden die by defining pixel intensity thresholds for each pixel in an image. In macro defect inspection, if, upon evaluation, pixel intensity values are found to fall outside of the range defined by the thresholds, those pixels are deemed to be defective. The thresholds themselves may be as simple as a standard deviation calculated from a golden die, but more often include weighting factors that take into consideration various features, variations and characteristics of a substrate S and the user defined criteria that apply to the product formed thereon. It is to be understood that models used for defect inspection may be formed in myriad ways and may or may not be based on a golden die in any way, the only requirement for macro defect inspection models being that the resulting inspection yields results that are satisfactory to the user of the system 8. Where macro defect inspection is to be carried out, a suitable model for such inspection may be obtained (step 64) at more or less the same time that a golden die is generated. As indicated by arrow 65, the formation of a model may in some instances use golden die information. Once a model has been created, subsequently captured images are compared with the model to identify defects (step 72).

The golden die image obtained in the previous step is used to remove the background of images captured during inspection for defocus defects, resulting in what is referred to as a differential image (step 66). The differential image consists of the differences between individual corresponding pixel values of the golden die image and an image of a die under inspection. The pixel intensity values that make up the differential image, which can be positive, negative or zero, are summed and averaged over the entire differential image (step 68). The resulting averaged values are then compared with similar averages obtained from inspecting an FEM to determine whether the averaged values cross a predetermined threshold set by a user of the system. In some embodiments it is possible that FEM-derived differential image average values may be directly compared with inspection derived differential image average values to determine whether an unacceptable level of defocus defects are present in a die.

As is understood by those skilled in the art, the polarizer 12 and analyzer 14 may be arranged angularly with respect to one another so as to prevent the passage of substantially all light or to permit the passage of substantially all light. In one embodiment of the present invention, the polarizer 12 and analyzer 14 are arranged angularly with respect to one another so as to prevent the passage of substantially all light $E_1$ and $E_2$ therethrough. In this embodiment, and where the substrate S did not affect the polarization state of the reflected light, the optical sensor 16 would register substantially no image. However, since the presence of features that modify polarity are generally present on the substrate S and because at least some degree of defocus defects are typically present, light $E_3$ and $E_4$ will be incident upon the optical sensor 16.

The angular positioning of the polarizer 12 with respect to the analyzer 14 will most often depend on the nature of the substrate S being inspected, though other factors may be used, including, but not limited to the nature of the light source 12, physical properties of the optical system and the like. In one embodiment, the polarization angle of the polarizer 12 is about 45° to the linear structures present on the substrate S being inspected. Accordingly, it is to be recognized that in some embodiments, the polarization angle of the analyzer 14 may vary depending on the nature of the substrate being inspected.

In some embodiments, a multiple scan inspection will be used to determine the presence of defects on a substrate S. In one embodiment, a first pass is undertaken with the polarizer 12 and analyzer 14 in a setting that passes insufficient light for macro defect inspection. This first pass is intended only to determining whether defocus or exposure defects exist in the imaged area of the substrate, generally one or more die or stepper shots. A second pass involves finding macro defects such as chips, cracks, particles, voids and scratches and is undertaken with the polarizer 12 and analyzer 14 arranged in a manner that allows a greater amount of light to pass therethrough.

In another embodiment, the system 8 may be used to detect changes in the thickness of, or the presence of, thin films on a substrate. In some instances, unwanted residual films will remain on all or portions of a substrate S after a processing step. Where properly arranged, differential images of a substrate 8 will identify the location and extent of residual films.

CONCLUSION

Although specific embodiments of the present invention have been illustrated and described herein, it will be appreciated by those of ordinary skill in the art that any arrangement that is calculated to achieve the same purpose may be substituted for the specific embodiments shown. Many adaptations of the invention will be apparent to those of ordinary skill in the art. Accordingly, this application is intended to cover any adaptations or variations of the invention. It is manifestly intended that this invention be limited only by the following claims and equivalents thereof.

What is claimed is:

1. A method of inspecting a substrate for exposure and defocus defects comprising:
    providing an inspection system comprising:
        a light source arranged to direct light onto a substrate;
        a first polarizing filter positioned between the light source and the substrate;
        an optical sensor arranged to receive light reflected from the substrate; and
        a second polarizing filter positioned between the substrate and the optical sensor;
        wherein a relative angle between the first and second polarizing filters is variable;
    arranging the first and second polarizing filters at a selected relative angle with respect to one another;
    capturing images of the substrate; and
    generating comparative data from the images to identify the existence of at least one of an exposure and a defocus defect on the substrate.

2. The method of inspecting a substrate of claim 1, further comprising rotating the first and second polarizing filters together to an inspection angle relative to the substrate whilst maintaining the selected relative angle therebetween.

3. The method of inspecting a substrate of claim 1, wherein processing the images comprises:
    generating a differential image for each captured image;
    averaging pixel intensity differences of the respective differential images over the entire differential image to obtain an average image intensity for each differential image;
    evaluating the average image intensity of each captured image with respect to a predetermined threshold to determine the existence of at least one of exposure and defocus defects on the substrate, if any.

4. The method of inspecting a substrate of claim 1, comprising:
    calibrating the output of the optical sensor with respect to known levels of at least one of an exposure and a defocus defect in a substrate.

5. The method of inspecting a substrate of claim 4, wherein calibrating comprises:
- capturing a plurality of images of a calibration substrate, each image being subject to a known degree of defocus and exposure defects;
- generating a differential image for each captured image;
- averaging pixel intensity differences of the differential images over the entire differential image to obtain an average image intensity; and
- recording the average image intensity values for each captured image having a known degree of defocus and exposure defect.

6. The method of inspecting a substrate of claim 3, wherein generating a differential image comprises averaging a plurality of captured images on a pixel by pixel basis to obtain an averaged image, which averaged imaged is subtracted from each captured image, on a pixel by pixel basis to produce a differential image.

7. The method of inspecting a substrate of claim 1, further comprising inspecting each captured image for defects selected from a group consisting of pits, voids, chips, cracks, particles, and scratches.

8. The method of inspecting a substrate of claim 7, wherein the inspection for defects selected from a group consisting of pits, voids, chips, cracks, particles, and scratches takes place substantially simultaneously as the inspection for at least one of exposure and defocus defects.

9. The method of inspecting a substrate of claim 6, further comprising inspecting the differential image to identify layer boundaries therein.

10. The method of inspecting a substrate of claim 2, wherein the first and second polarizing filters are rotated relative to the substrate through a plurality of inspection angles while maintaining the selected relative angle.

11. The method of inspecting a substrate of claim 10, further comprising:
- determining a desired inspection angle of the first and second polarizing filters relative to the substrate from the plurality of inspection angles based upon a contrast in intensity of reflected light in corresponding captured images, the desired inspection angle selected to promote identification of the existence of the at least one of an exposure and a defocus defect on the substrate.

* * * * *

UNITED STATES PATENT AND TRADEMARK OFFICE
CERTIFICATE OF CORRECTION

PATENT NO. : 7,586,607 B2
APPLICATION NO. : 11/678407
DATED : September 8, 2009
INVENTOR(S) : Gang Sun It is certified that error appears in the above-identified patent and that said Letters Patent is hereby corrected as shown below:

Title Page, Column 2 (Abstract), line 1, after "inspection" insert --of--.

Column 7, line 9-20, delete "Upon reflection,......substrate S." and insert the same after "angle $\theta$." on Col. 7, line 8, as a continuation of the same paragraph.

Column 10-11, line 66-67 (Col. 10) 1-22 (Col. 11), delete "Similarly,......72)." and insert the same after "(step 62)." on Col. 10, line 65, as a continuation of the same paragraph.

Signed and Sealed this

Tenth Day of November, 2009

David J. Kappos
*Director of the United States Patent and Trademark Office*